(12) United States Patent
Newkirk et al.

(10) Patent No.: US 10,135,127 B2
(45) Date of Patent: Nov. 20, 2018

(54) SYSTEM AND APPARATUS FOR DRIVING ANTENNA

(71) Applicant: ViaSat, Inc., Carlsbad, CA (US)

(72) Inventors: Jack C. Newkirk, Woodstock, GA (US); B. Wayne Holt, Dacula, GA (US); Bradley H. Smith, Cumming, GA (US); Kevin M. Skinner, Gainesville, GA (US); E. Mitchell Blalock, Dunwoody, GA (US)

(73) Assignee: Viasat, Inc., Carlsbad, CA (US)

( * ) Notice: Subject to any disclaimer, the term of this patent is extended or adjusted under 35 U.S.C. 154(b) by 0 days.

(21) Appl. No.: 15/582,398

(22) Filed: Apr. 28, 2017

(65) Prior Publication Data

US 2017/0237155 A1   Aug. 17, 2017

Related U.S. Application Data

(63) Continuation of application No. 14/752,232, filed on Jun. 26, 2015, now Pat. No. 9,680,199.
(Continued)

(51) Int. Cl.
*H01Q 1/28* (2006.01)
*H01Q 1/12* (2006.01)
(Continued)

(52) U.S. Cl.
CPC ............ *H01Q 1/288* (2013.01); *H01Q 1/125* (2013.01); *H01Q 3/08* (2013.01);
(Continued)

(58) Field of Classification Search
CPC .......... H01Q 1/288; H01Q 1/125; H01Q 3/08; H04B 7/18515; H04B 7/18519; H04B 7/18508
(Continued)

(56) References Cited

U.S. PATENT DOCUMENTS

| 4,134,307 A | 1/1979 | Nilsson |
| 5,508,712 A | 4/1996 | Tom |

(Continued)

FOREIGN PATENT DOCUMENTS

| WO | WO 2007066885 A1 | 6/2007 |
| WO | WO 2015200860 A1 | 12/2015 |

OTHER PUBLICATIONS

PCT/2015/038121 International Search Report and Written Opinion of the ISA, 11 pgs.
(Continued)

*Primary Examiner* — Hai V Nguyen
(74) *Attorney, Agent, or Firm* — Holland & Hart LLP

(57) ABSTRACT

A multiple-antenna positioning system with a single drive element, providing reduced weight and complexity over systems that have a drive element for each antenna. In certain examples, each antenna can be coupled with a rotating spindle, with each antenna spindle being coupled with a pair of link arms. By driving a single drive spindle, each of the antenna spindles in the system can be rotated by the associated pair of link arms. The link arms can have an adjustable length, such as through a turnbuckle mechanism, to reduce backlash in the system, and in some examples can apply a preload to the system. By reducing backlash, the multiple antenna positioning system can have improved responsiveness to a rotation of the single drive element, as well as improved stability of the positioning of each antenna when the drive element is held in a fixed position.

25 Claims, 8 Drawing Sheets

Related U.S. Application Data

(60) Provisional application No. 62/018,376, filed on Jun. 27, 2014.

(51) Int. Cl.
*H04B 7/185* (2006.01)
*H01Q 3/08* (2006.01)

(52) U.S. Cl.
CPC ..... *H04B 7/18515* (2013.01); *H04B 7/18519* (2013.01); *H04B 7/18508* (2013.01)

(58) Field of Classification Search
USPC .......................................................... 455/9
See application file for complete search history.

(56) References Cited

U.S. PATENT DOCUMENTS

| | | | |
|---|---|---|---|
| 5,864,321 A | 1/1999 | Paul | |
| 5,909,564 A * | 6/1999 | Alexander | H04L 49/351 710/316 |
| 5,952,980 A | 9/1999 | Boling | |
| 6,052,560 A | 4/2000 | Karabinis | |
| 6,163,539 A * | 12/2000 | Alexander | H04L 12/56 370/389 |
| 6,195,060 B1 * | 2/2001 | Spano | H01Q 1/28 248/183.1 |
| 6,204,823 B1 * | 3/2001 | Spano | H01Q 1/125 343/705 |
| 6,310,582 B1 | 10/2001 | Uetake et al. | |
| 6,403,125 B1 | 6/2002 | Pauly | |
| 6,486,845 B2 * | 11/2002 | Ogawa | H01Q 1/42 343/757 |
| 6,661,388 B2 | 12/2003 | Desargant et al. | |
| 6,670,317 B2 | 12/2003 | Severns | |
| 6,738,024 B2 * | 5/2004 | Butler | H01Q 1/28 343/757 |
| 6,741,573 B1 | 5/2004 | Asaeda | |
| 6,812,904 B2 * | 11/2004 | Tietjen | H01Q 3/08 343/757 |
| 6,839,039 B2 * | 1/2005 | Tanaka | H01P 3/10 343/757 |
| 6,882,321 B2 * | 4/2005 | Tietjen | H01Q 3/08 343/757 |
| 6,911,950 B2 * | 6/2005 | Harron | H01Q 3/08 343/765 |
| 6,952,587 B2 * | 10/2005 | Whikehart | H04W 64/00 455/19 |
| 6,999,036 B2 * | 2/2006 | Stoyanov | H01Q 1/1264 343/757 |
| 7,123,876 B2 | 10/2006 | Wang et al. | |
| 7,183,989 B2 * | 2/2007 | Tietjen | G01S 7/03 343/757 |
| 7,183,996 B2 * | 2/2007 | Wensink | H01Q 1/125 343/882 |
| 7,199,764 B2 * | 4/2007 | Tietjen | G01S 7/03 343/757 |
| 7,245,262 B2 * | 7/2007 | Kim | H01Q 1/246 343/757 |
| 7,256,748 B2 * | 8/2007 | Tietjen | H01Q 3/08 343/763 |
| 7,385,562 B2 * | 6/2008 | Stoyanov | H01Q 1/1264 343/757 |
| 7,388,562 B2 * | 6/2008 | Koyama | G09G 3/3233 345/76 |
| 7,394,779 B2 | 7/2008 | Seo et al. | |
| 7,595,762 B2 * | 9/2009 | Mansour | H01Q 1/3283 343/757 |
| 7,616,165 B2 * | 11/2009 | Tammisetti | H01Q 3/04 343/776 |
| 7,629,935 B2 * | 12/2009 | Mansour | H01Q 3/04 343/757 |
| 7,663,566 B2 * | 2/2010 | Engel | H01Q 21/064 343/700 MS |
| 7,710,337 B2 * | 5/2010 | Blalock | H01Q 1/125 310/90.5 |
| 7,893,885 B2 * | 2/2011 | Jung | H01Q 3/08 343/757 |
| 7,911,400 B2 * | 3/2011 | Kaplan | H01Q 1/125 343/713 |
| 7,969,375 B2 * | 6/2011 | Blalock | H01Q 1/125 343/757 |
| 8,013,798 B2 * | 9/2011 | Blalock | H01Q 1/125 343/757 |
| 8,054,233 B2 * | 11/2011 | Holt | H01Q 3/08 343/757 |
| 8,085,211 B2 * | 12/2011 | Yang | H01Q 1/246 343/758 |
| 8,120,541 B2 * | 2/2012 | Jung | H01Q 1/1257 343/765 |
| 8,178,246 B2 | 5/2012 | Shima | |
| 8,638,264 B2 * | 1/2014 | Hall | H01Q 21/061 343/757 |
| 8,761,663 B2 * | 6/2014 | Kaplan | H01Q 3/04 342/74 |
| 8,964,891 B2 * | 2/2015 | Tsofe | H01Q 3/267 375/296 |
| 9,016,631 B2 * | 4/2015 | Parsley | B64C 1/1446 244/129.5 |
| 9,263,797 B1 * | 2/2016 | Hall | H01Q 3/02 |
| 9,444,149 B2 * | 9/2016 | Cha | H01P 1/161 |
| 9,553,657 B2 * | 1/2017 | Cordone | H04B 7/18508 |
| 9,583,829 B2 * | 2/2017 | Engel | H01Q 3/08 |
| 9,590,299 B2 * | 3/2017 | Rao | H01Q 3/20 |
| 9,680,199 B2 * | 6/2017 | Newkirk | H01Q 1/125 |
| 9,686,027 B2 * | 6/2017 | Yeshanov | H04B 17/40 |
| 9,711,850 B2 * | 7/2017 | Naym | H01Q 3/08 |
| 9,882,276 B1 * | 1/2018 | Hall | H01Q 3/08 |
| 9,917,362 B2 * | 3/2018 | Zimmerman | H01Q 3/08 |
| 2002/0011958 A1 | 1/2002 | Ogawa et al. | |
| 2006/0132372 A1 | 6/2006 | Jung et al. | |
| 2008/0297426 A1 * | 12/2008 | Jung | H01Q 3/08 343/765 |
| 2009/0121932 A1 | 5/2009 | Whitehead et al. | |
| 2010/0265878 A1 | 10/2010 | Foxworthy et al. | |
| 2013/0342390 A1 * | 12/2013 | Cha | H01P 1/161 342/352 |
| 2015/0380802 A1 * | 12/2015 | Newkirk | H01Q 1/125 343/879 |

OTHER PUBLICATIONS

ISA/EPO—WO/ISA for International Appl. No. PCTUS2015038121, 8 pgs.

* cited by examiner

SYSTEM AND APPARATUS FOR DRIVING ANTENNA

CROSS REFERENCES

The present Application for Patent is a continuation of U.S. patent application Ser. No. 14/752,232 by Newkirk, et al., entitled "Systems and Apparatus for Driving Antenna," filed Jun. 26, 2015, which claims priority to U.S. Provisional Patent Application No. 62/018,376 by Newkirk et al., entitled "System and Apparatus for Driving Antenna," filed Jun. 27, 2014, which is expressly incorporated by reference herein.

BACKGROUND

Antenna systems can include multiple antennas in order to provide operation at multiple frequency bands. For example, in mobile applications where a user moves between coverage areas of different satellites operating at different frequency bands, each of the antennas may be used to individually communicate with one of the satellites. However, in some applications such as on an airplane, performance requirements and constraints such as size, cost and/or weight, may preclude the use of multiple antennas.

SUMMARY

Methods, systems, and devices are described for driving multiple antennas in a multiple antenna system. The multiple antenna system can include two or more antennas, each rotating on their own antenna spindle, with their positioning provided by a multiple-antenna positioner. The multiple-antenna positioner can be controlled in a first mode where a first antenna is positioned in order to establish and/or maintain a communications link with a satellite. In the first mode, a second antenna in the multiple antenna system may be in an inactive state without maintaining a communications link. The multiple-antenna positioner can alternatively be controlled in a second mode where the second antenna is positioned in order to establish and/or maintain a communications link with a satellite, which may or may not be the same satellite involved in the communications link of the first mode. In the second mode, the first antenna may be in an inactive state, without maintaining a communications link.

Each antenna spindle can be coupled with a drive spindle by a pair of link arms, such that rotation of the drive spindle simultaneously rotates each of the associated antenna spindles. In some examples the link arms can be adjusted in a manner that reduces a degree of backlash, such as an adjustment via a turnbuckle. By reducing the degree of backlash, the accuracy and responsiveness of the positioning of the multiple antennas can be improved. Reducing a degree of backlash can additionally include a mechanical preload of the system, where various components of the antenna system can be under a static tensile or compressive load. A preload can help to limit a degree of backlash over time, by compensating for wear of various components of the multiple antenna system. In various examples, the multiple antenna positioner can reduce size, cost, and/or weight in comparison to a system that has a unique positioner for each antenna, while also having suitable stiffness and/or drive efficiency for providing positioning of each of the associated antennas.

Further scope of the applicability of the described methods and apparatuses will become apparent from the following detailed description, claims, and drawings. The detailed description and specific examples are given by way of illustration only, since various changes and modifications within the scope of the description will become apparent to those skilled in the art.

BRIEF DESCRIPTION OF THE DRAWINGS

A further understanding of the nature and advantages of various aspects of the present disclosure may be realized by reference to the following drawings. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The described features generally relate to a multiple antenna system, and particularly a multiple-antenna positioner. In the multiple-antenna positioner, each antenna can be coupled with a rotating spindle, which may each be coupled with a single drive spindle by a pair of link arms. The link arms couple the spindles such that a rotation of the single drive spindle can provide a rotation of each of the antenna spindles. The link arms may have a fixed length, or may alternatively have a variable length by way of various mechanisms such as a turnbuckle. With a variable length, the link arms may be adjusted in length to reduce a degree of backlash in the system, where the backlash may be the result of gaps between various coupled components of the multiple-antenna positioner. Reducing the degree of backlash may further include applying a preload to the system, which can maintain the reduction in backlash over time by compensating for mechanical wear of various components. By reducing backlash in the multiple-antenna positioner, the multiple-antenna positioning system can have a favorable degree of stiffness, such that the positioning of each of the antennas can be more responsive to a rotation of the drive spindle, and can also be more stable when the drive spindle is held in a fixed position.

This description provides examples, and is not intended to limit the scope, applicability or configuration of embodiments of the principles described herein. Rather, the ensuing description will provide those skilled in the art with an enabling description for implementing embodiments of the principles described herein. Various changes may be made in the function and arrangement of elements.

Thus, various embodiments may omit, substitute, or add various procedures or components as appropriate. For instance, it should be appreciated that the methods may be performed in an order different than that described, and that various steps may be added, omitted or combined. Also, aspects and elements described with respect to certain embodiments may be combined in various other embodiments. It should also be appreciated that the following systems, methods, devices, and software may individually or collectively be components of a larger system, wherein other procedures may take precedence over or otherwise modify their application.

Figure 1:
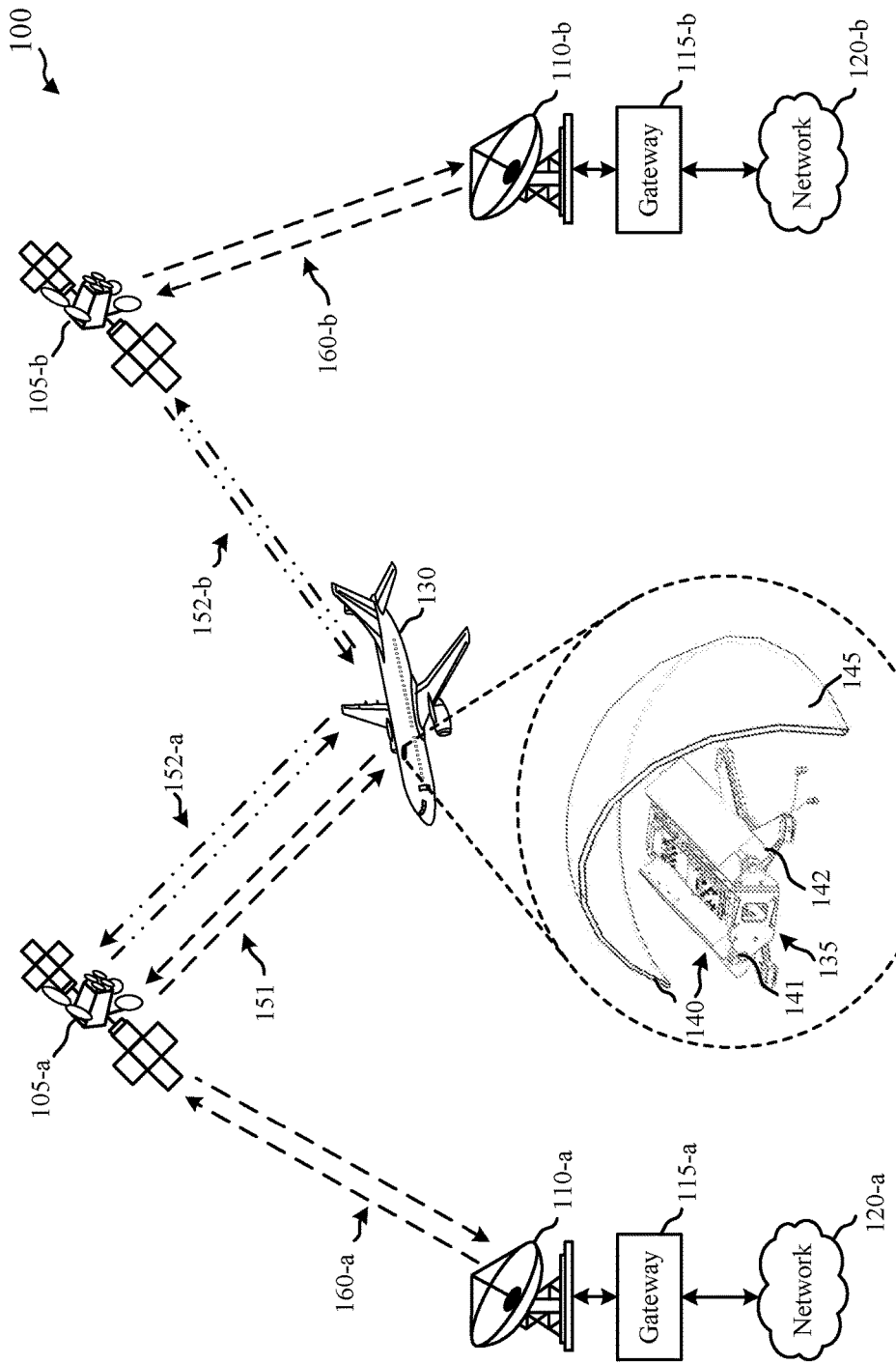
FIG. 1 shows a diagram of a satellite communication system in accordance with various aspects of the present disclosure.

FIG. 1 shows a diagram of a satellite communication system 100 in accordance with various aspects of the present disclosure. The satellite communication system 100 includes a first satellite 105-a, a first gateway 115-a, a first gateway antenna system 110-a, and an aircraft 130. The first gateway 115-a communicates with at least a first network 120-a. In operation, the satellite communication system 100 can provide for one-way or two-way communications between the aircraft 130 and the first network 120-a through at least the first satellite 105-a and the first gateway 115-a.

In some examples, the satellite communications system 100 includes a second satellite 105-b, a second gateway 115-b, and a second gateway antenna system 110-b. The second gateway 115-b may communicate with at least a second network 120-b. In operation, the satellite communication system 100 can provide for one-way or two-way communications between the aircraft 130 and the second network 120-b through at least the second satellite 105-b and the second gateway 115-b.

The first satellite 105-a and the second satellite 105-b may be any suitable type of communication satellite. In some examples, at least one of the first satellite 105-a and the second satellite 105-b may be in a geostationary orbit. In other examples, any appropriate orbit (e.g., low earth orbit (LEO), medium earth orbit (MEO), etc.) for the first satellite 105-a and/or the second satellite 105-b may be used. The first satellite 105-a and/or the second satellite 105-b may be a multi-beam satellite configured to provide service for multiple service beam coverage areas in a predefined geographical service area. In some examples, the first satellite 105-a and the second satellite 105-b may provide service in non-overlapping coverage areas, partially-overlapping coverage areas, or fully-overlapping coverage areas. In some examples, the satellite communication system 100 includes more than two satellites 105.

The first gateway antenna system 110-a may be one-way or two-way capable and designed with adequate transmit power and receive sensitivity to communicate reliably with the first satellite 105-a. The first satellite 105-a may communicate with the first gateway antenna system 110-a by sending and receiving signals through one or more beams 160-a. The first gateway 115-a sends and receives signals to and from the first satellite 105-a using the first gateway antenna system 110-a. The first gateway 115-a is connected to the first network 120-a. The first network 120-a may include a local area network (LAN), metropolitan area network (MAN), wide area network (WAN), or any other suitable public or private network and may be connected to other communications networks such as the Internet, telephony networks (e.g., Public Switched Telephone Network (PSTN), etc.), and the like.

Examples of satellite communications system 100 may include the second satellite 105-b, along with either unique or shared associated system components. For example, the second gateway antenna system 110-b may be one-way or two-way capable and designed with adequate transmit power and receive sensitivity to communicate reliably with the second satellite 105-b. The second satellite 105-b may communicate with the second gateway antenna system 110-b by sending and receiving signals through one or more beams 160-b. The second gateway 115-b sends and receives signals to and from the second satellite 105-b using the second gateway antenna system 110-b. The second gateway 115-b is connected to the second network 120-b. The second network 120-b may include a local area network (LAN), metropolitan area network (MAN), wide area network (WAN), or any other suitable public or private network and may be connected to other communications networks such as the Internet, telephony networks (e.g., Public Switched Telephone Network (PSTN), etc.), and the like.

In various examples, the first network 120-a and the second network 120-b may be different networks, or the same network 120. In various examples, the first gateway 115-a and the second gateway 115-b may be different gateways, or the same gateway 115. In various examples, the first gateway antenna system 110-a and the second gateway antenna system 110-b may be different gateway antenna systems, or the same gateway antenna system 110.

The aircraft 130 can employ a communication system including a multiple antenna system 140. The multiple antenna system 140 can include, for instance a first antenna 141 and a second antenna 142. In some examples, the first antenna 141 and/or the second antenna 142 can be a dual polarized planar horn antenna array. Alternatively, the first antenna 141 and/or the second antenna 142 can be a different type of antenna. The multiple antenna system 140 can be mounted on the outside of the fuselage of the aircraft 130 under a radome 145. The multiple antenna system 140 may be mounted to an antenna assembly positioning system 135 used to point either the first antenna 141, or the second antenna 142 to a satellite 105 (e.g., actively tracking) during operation. In some examples, antenna assembly positioning system 135 can include both a system to control an azimuth orientation of an antenna, and a system to control an elevation orientation of an antenna.

The first antenna 141 and/or the second antenna 142 may operate in the International Telecommunications Union (ITU) Ku, K, or Ka-bands, for example from approximately 17 to 31 Giga-Hertz (GHz). Alternatively, the first antenna 141 and/or the second antenna 142 may operate in other frequency bands such as C-band, X-band, S-band, L-band, and the like. In various examples, the first antenna 141 and the second antenna 142 may be configured to operate in different frequency bands, or in the same frequency band. In a particular example, the first antenna 141 can be configured to operate at Ku-band (e.g. receiving signals between 10.95 and 12.75 GHz, and transmitting signals between 14.0 to 14.5 GHz), and the second antenna 142 can be configured to operate at Ka-band (e.g. receiving signals between 17.7 and 21.2 GHz, and transmitting signals between 27.5 to 31.0 GHz).

In some examples of the satellite communications system 100, the first antenna 141 can be associated with the first satellite 105-a, and the second antenna 142 can be associated with the second satellite 105-b. In operation, the aircraft 130 can have a location that is within a coverage area of the first satellite 105-*a* and/or within a coverage area of the second satellite 105-*b*, and communications with either the first antenna 141 or the second antenna 142 can be selected based at least in part on the position of the aircraft 130. For instance, in a first mode of operation, while the aircraft 130 is located within a coverage area of the first satellite 105-*a*, the aircraft 130 can use the first antenna 141 of the multiple antenna system 140 to communicate with the first satellite 105-*a* over one or more first beams 151. In the first mode of operation, the second antenna 142 can be in an inactive state without maintaining a communications link with a satellite. In a second mode of operation, while the aircraft 130 is located within a coverage area of the second satellite 105-*b*, the aircraft 130 can use the second antenna 142 of the multiple antenna system 140 to communicate with the second satellite 105-*b* over one or more second beams 152-*b*. The second mode can be selected, for instance, in response to the aircraft 130 entering a coverage area of the second satellite 105-*b*, and/or leaving a coverage area of the first satellite 105-*a*. In examples where the aircraft is located within an overlapping coverage area of both the first satellite 105-*a* and the second satellite 105-*b*, the second mode can be selected based on other factors, such as network availability, communication capacity, communication costs, signal strength, signal quality, and the like. In the second mode of operation, the first antenna 141 can be in an inactive state without maintaining a communications link with a satellite In other examples of the satellite communications system 100, the first antenna 141 and the second antenna 142 can both be associated with the first satellite 105-*a*. In the first mode of operation the aircraft 130 can use the first antenna 141 to communicate with the first satellite 105-*a* over one or more first beams 151, and in an alternate example of the second mode of operation, the aircraft 130 can use the second antenna 142 to communicate with the first satellite 105-*a* over one or more second beams 152-*a*. The alternate example of the second mode can be selected, for instance, in the event of an error condition, a fault condition, or a degradation of the first antenna 141, where the second antenna 142 can provide backup communications. Additionally or alternatively, the alternate example of the second mode can be selected to change from a first frequency band and/or communications protocol associated with the first antenna 141 to a second frequency band and/or communications protocol associated with the second antenna 142.

The communication system of the aircraft 130 can provide communication services for communication devices within the aircraft 130 via a modem (not shown). Communication devices may utilize the modem to connect to and access at least one of the first network 120-*a* or the second network 120-*b* via the multiple antenna system 140. For example, mobile devices may communicate with at least one of the first network 120-*a* or the second network 120-*b* via network connections to modem, which may be wired or wireless. A wireless connection may be, for example, of a wireless local area network (WLAN) technology such as IEEE 802.11 (Wi-Fi), or other wireless communication technology.

The size of the multiple antenna system 140 may directly impact the size of the radome 145, for which a low profile may be desired. In other examples, other types of housings are used with the multiple antenna system 140. Additionally, the multiple antenna system 140 may be used in other applications besides onboard the aircraft 130, such as onboard boats, automobiles or other vehicles, or on ground-based stationary systems.

Figure 2A:
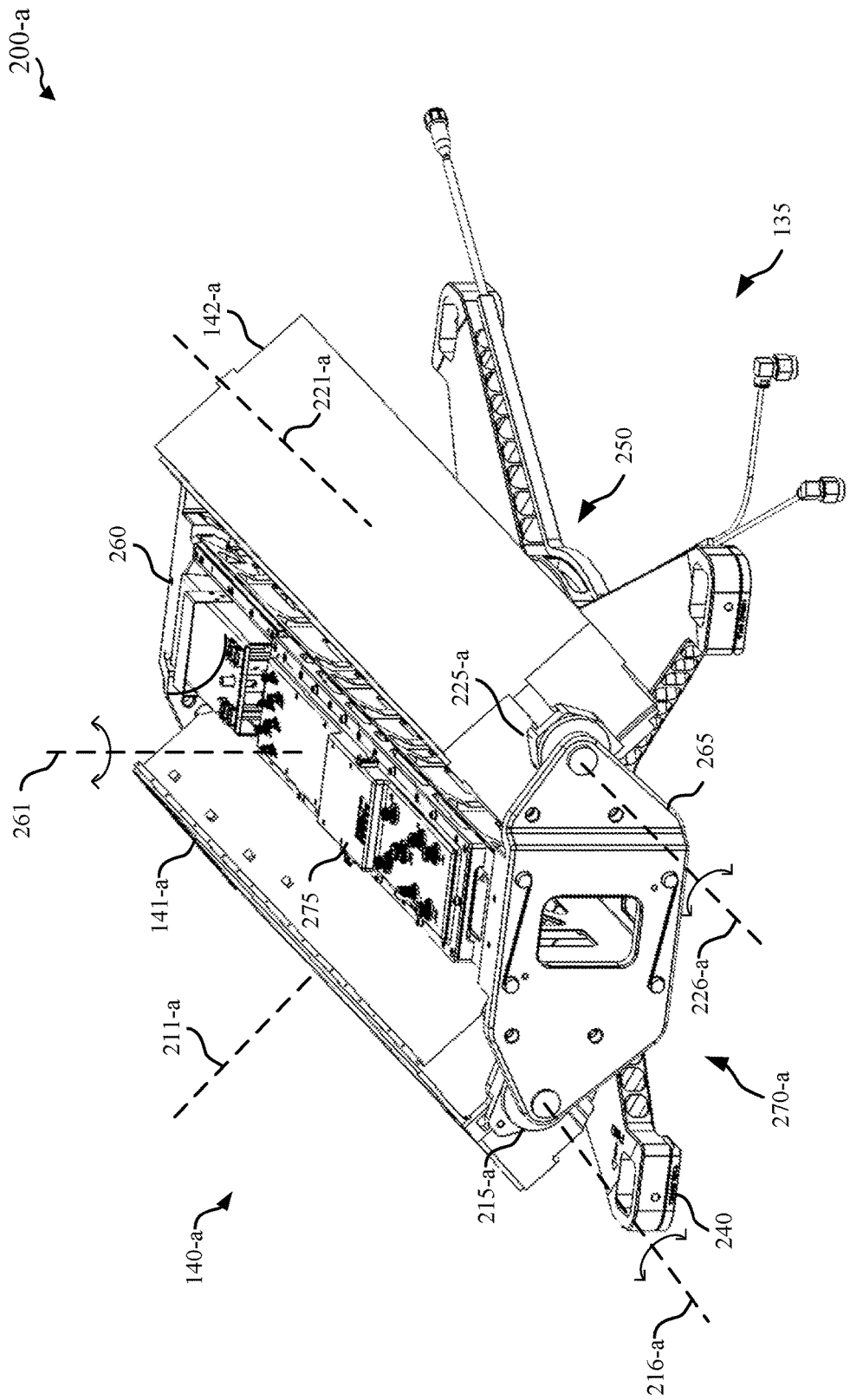
FIG. 2A shows a view of a multiple antenna system in accordance with various aspects of the present disclosure.

FIG. 2A shows a view 200-*a* of a multiple antenna system 140-*a* in accordance with various aspects of the present disclosure. As shown in view 200-*a*, the multiple antenna system 140-*a* includes a first antenna 141-*a*, and a second antenna 142-*a*. The first antenna 141-*a* can have a first antenna boresight 211-*a*, which corresponds to the direction of maximum gain of the first antenna 141-*a*. The first antenna 141-*a* is coupled with a first spindle 215-*a* rotating about a first spindle axis 216-*a*. In some examples, rotation of the first spindle 215-*a* about the first spindle axis 216-*a* may provide an elevation adjustment to the first antenna boresight 211-*a*. The second antenna 142-*a* can have a second antenna boresight 221-*a*, which corresponds to the direction of maximum gain of the second antenna 142-*a*. The second antenna 142-*a* is coupled with a second spindle 225-*a* rotating about a second spindle axis 226-*a*. In some examples, rotation of the second spindle 225-*a* about the second spindle axis 226-*a* may provide an elevation adjustment to the second antenna 142-*a*.

The first spindle 215-*a* and the second spindle 225-*a* can be rotatably coupled with a spindle support structure 265 by one or more rotating bearings associated with each of the first spindle 215-*a* and the second spindle 225-*a*. In some examples the support provided by the spindle support structure 265 can rigidly fix the locations of the first spindle axis 216-*a* and the second spindle axis 226-*a*. In other examples the first spindle axis 216-*a* and the second spindle axis 226-*a* may move with respect to the spindle support structure 265, by way of a compliant coupling and/or a kinematic linkage between the first spindle 215-*a* and/or the second spindle 225-*a* and spindle support structure 265.

The multiple antenna system 140-*a* may be mounted to the aircraft 130 by way of a base element 240. The multiple antenna system 140-*a* may further include an antenna assembly positioning system 135, including, for example, an azimuth drive 250 and a multiple-antenna positioner 270-*a*. The azimuth drive 250 can provide rotation of an azimuth base 260 about an azimuth axis 261, and the multiple-antenna positioner 270-*a* can simultaneously provide rotation of the first spindle 215-*a* about the first spindle axis 216-*a*, and the second spindle 225-*a* about the second spindle axis 226-*a* to provide adjustment in elevation. In some examples the spindle support structure 265 can be one or more removable portions of an azimuth base 260, and in other examples the spindle support structure 265 can be a portion of an azimuth base 260 formed as a single workpiece.

In a first mode of operation of the multiple antenna system 140-*a*, a rotation of the azimuth base 260 about the azimuth axis 261, in combination with a rotation of the first spindle 215-*a* about the first spindle axis 216-*a*, can direct the first antenna boresight 211-*a* towards a satellite 105. In a second mode of operation, a rotation of the azimuth base 260 about the azimuth axis 261, in combination with a rotation of the second spindle 225-*a* about the second spindle axis 226-*a*, can direct the second antenna boresight 221-*a* towards a satellite 105. When configured in this manner, a single drive element of the multiple-antenna positioner 270-*a* can provide adjustment to both the first antenna 141-*a* and the second antenna 142-*a*. Compared to single antenna systems, this configuration can provide benefits including the support of multiple frequency bands or the availability of redundant antennas. Compared to multiple antenna systems that have a drive element for each antenna, this configuration can provide benefits including reduced cost, reduced weight, and reduced complexity.

The antenna assembly positioning system 135 is responsive to commands from an antenna control unit 275 to simultaneously position the first antenna 141-*a* and the second antenna 142-*a* to direct either the first antenna boresight 211-*a* or the second antenna boresight 221-*a* towards a target. In addition, the commands from the antenna control unit 275 can be used to control whether the first antenna 141-*a* or the second antenna 142-*a* is used to communicate one or more signals between the multiple antenna system 140-*a* and the target. In other words, the antenna assembly positioning system 135 points one of the first antenna 141-*a* and the second antenna 142-*a* at the target to provide communication between the multiple antenna system 140-*a* and the target, while the other of the first antenna 141-*a* and the second antenna 142-*a* points in a direction other than the target and is not used for communication. The multiple antenna system 140-*a* may also include additional components to facilitate communication of the signals. The components of the antenna control unit 275 can include processor(s), storage device(s), input device(s), output device(s), communication systems, data buses and working memory, which can include operating systems and applications/programs. Although illustrated as part of multiple antenna assembly 140-*a*, aspects of the antenna control unit 275 may be implemented in components external to the multiple antenna assembly 140-*a*, such as within a modem or other control unit located, for example, within the fuselage of an aircraft.

Figure 2B:
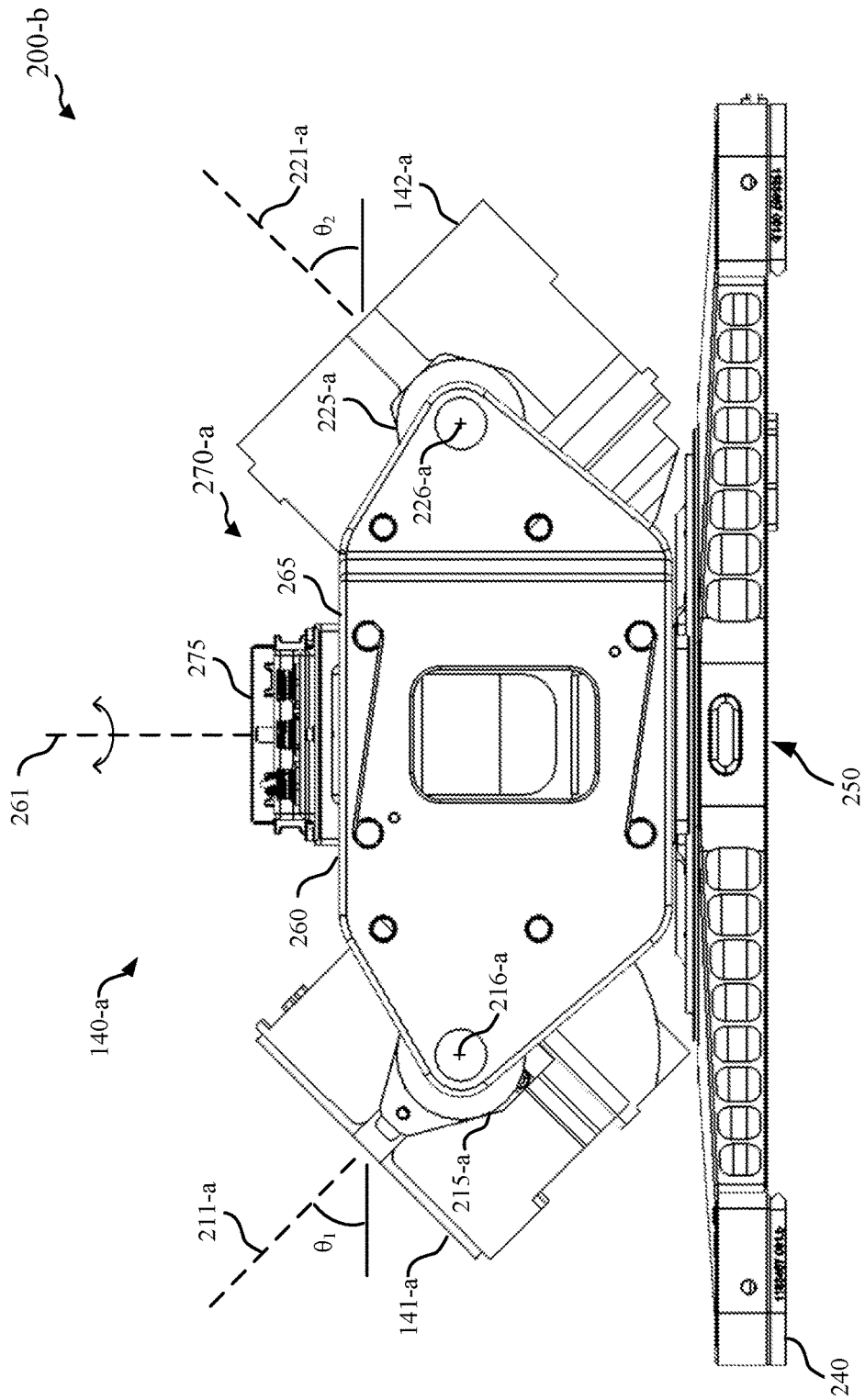
FIG. 2B shows a view of the multiple antenna system in accordance with various aspects of the present disclosure.

FIG. 2B shows a view 200-*b* of the multiple antenna system 140-*a* in accordance with various aspects of the present disclosure. View 200-*b* shows multiple antenna system 140-*a* as seen in line with the first spindle axis 216-*a*. As shown, the first antenna boresight 211-*a* is in the plane of the view, and has a first nominal elevation angle $\theta_1$. In some examples, such as the example shown in FIG. 2B, the second spindle axis 226-*a* can be parallel to the first spindle axis 216-*a*. In such an example, as shown, the second antenna boresight 221-*a* is also in the plane of the view, and can have a second nominal elevation angle $\theta_2$. In various examples, the first nominal elevation angle $\theta_1$ and the second nominal elevation angle of $\theta_2$. can be the same angle, or can be different angles. Therefore, in some examples the first nominal elevation angle $\theta_1$ and the second nominal elevation angle $\theta_2$ can be configured such that the first antenna boresight 211-*a* and the second antenna boresight 221-*a* are non-parallel. In some examples, the first nominal elevation angle $\theta_1$ and the second nominal elevation angle $\theta_2$ can be configured such that the first antenna boresight 211-*a* and the second antenna boresight 221-*a* are separated by a particular angle (e.g., 90 degrees, etc.).

In the illustrated example, where the first spindle axis 216-*a* and the second spindle axis 226-*a* are parallel, and the first antenna boresight 211-*a* and the second antenna boresight 221-*a* are perpendicular to their respective spindle axes, the first antenna boresight 211-*a* and the second antenna boresight 221-*a* can be separated by 180 degrees with respect to an azimuth axis 261. Said a different way, the projection of the first antenna boresight 211-*a* and the projection of the second antenna boresight 221-*a* on to a plane perpendicular to the azimuth axis 261 can be separated by 180 degrees. In other examples, the first antenna boresight 211-*a* and the second antenna boresight 221-*a* can be separated by some other angle with respect to an azimuth axis.

The multiple-antenna positioner 270-*a* can have a single drive element that simultaneously adjusts the first antenna boresight 211-*a* and the second antenna boresight 221-*a*. In some examples, the multiple-antenna positioner 270-*a* can be configured in a manner such that an increase in an elevation angle of the first antenna boresight 211-*a* has a corresponding decrease in an elevation angle of the second antenna boresight 221-*a*, or vice-versa. In other examples, the multiple-antenna positioner 270-*a* can be configured in a manner where an elevation angle of the first antenna boresight 211-*a* and an elevation angle of the second antenna boresight 221-*a* can both increase or both decrease in response to the drive element. This can be true, for instance, where the nominal elevation angle of the first antenna boresight 211-*a* and the nominal elevation angle of the second antenna boresight 221-*a* are 90 degrees, and elevation angle is considered to be an absolute value with respect to a horizontal plane. This can also be the case where the nominal elevation angle of the first antenna boresight 211-*a* and the nominal elevation angle of the second antenna boresight 221-*a* are measured from the same azimuth direction (as opposed to having a separation of 180 degrees with respect to an azimuth axis as shown in FIG. 2B). Furthermore, an elevation angle of the first antenna boresight 211-*a* and an elevation angle of the second antenna boresight 221-*a* can both increase or both decrease in response to the drive element by way of an additional linkage and/or gearing which causes the first spindle 215-*a* and the second spindle 225-*a* to rotate in opposite directions.

Figure 3A:
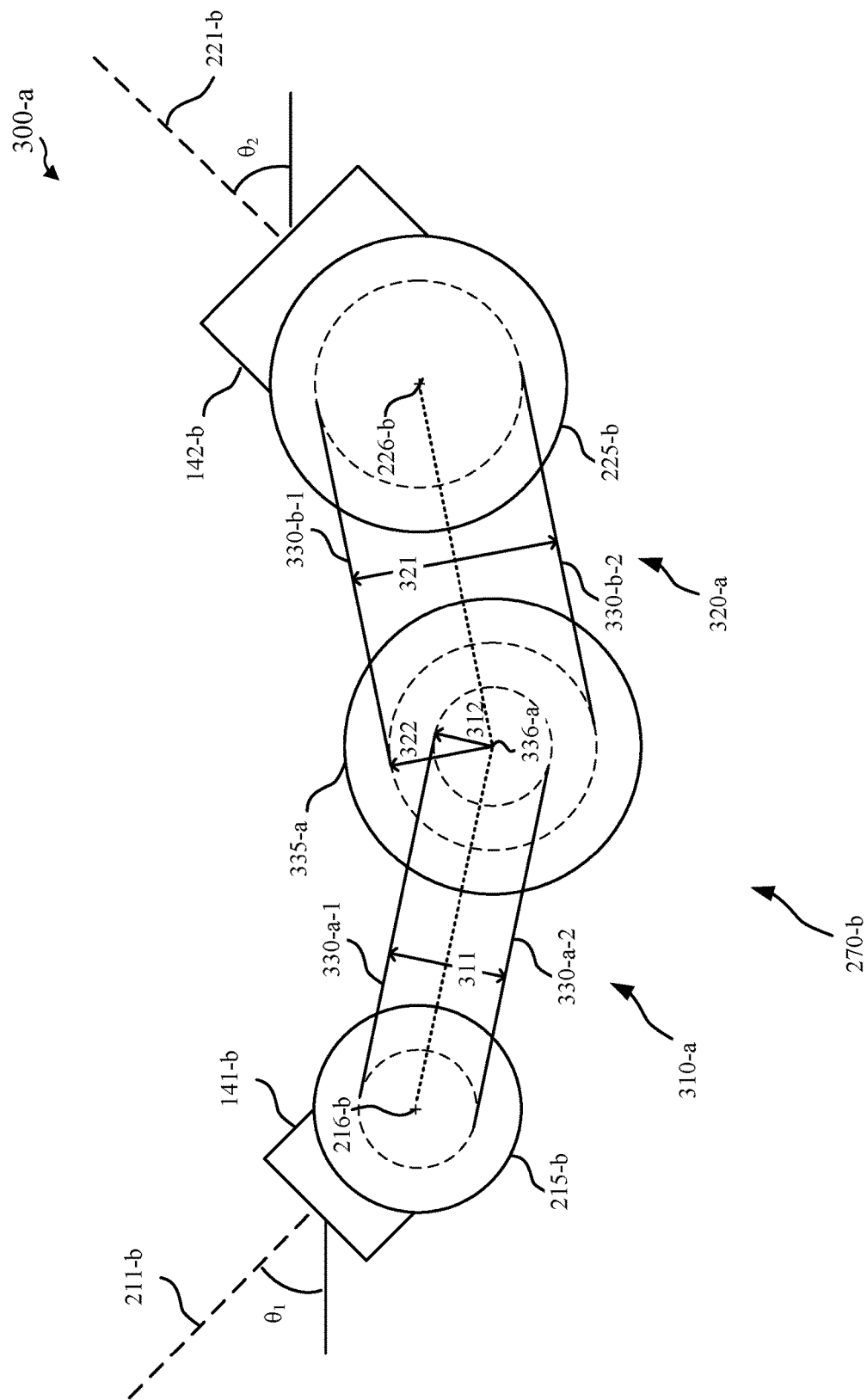
FIG. 3A shows a schematic view of a first state of a multiple-antenna positioner in accordance with various aspects of the present disclosure.

FIG. 3A shows a schematic view of a first state 300-*a* of a multiple-antenna positioner 270-*b* in accordance with various aspects of the present disclosure. The multiple-antenna positioner 270-*b* includes a first spindle 215-*b* which is coupled with a first antenna 141-*b*, and a second spindle 225-*b* which is coupled with a second antenna 142-*b*. The multiple-antenna positioner 270-*b* further includes a third spindle 335-*a*, which rotates about a third spindle axis 336. The first spindle 215-*b*, the second spindle 225-*b*, and the third spindle 335-*a* can all be rotatably coupled, for example, to a spindle support structure such as spindle support structure 265 described in reference to FIGS. 2A and 2B (omitted here for clarity). As previously described, in various examples the spindle support structure may provide fixed relative locations between any of the first spindle axis 216-*b*, the second spindle axis 226-*b*, and the third spindle axis 336-*a*, or may provide relative movement between any of the first spindle axis 216-*b*, the second spindle axis 226-*b*, and the third spindle axis 336-*a* by way of a compliant member or a kinematic linkage.

The third spindle 335-*a* is further coupled with a drive element. The drive element may include any element suitable for rotating the third spindle 335-*a*, which in some examples may include a motor, and may further include a gearbox. The motor may be any motor suitable for providing a rotation of the third spindle 335-*a*, including an AC electric motor, a DC electric motor, a hydraulic motor, or any other suitable motor. The gearbox, where included in the drive system, may be any mechanism suitable for providing a mechanical ratio between the motor and the third spindle 335-*a*, any may include any of a bevel gear, a helical gear, a worm gear, a clutch, a hydraulic transmission, and any other suitable mechanism. In some examples the motor and the gearbox can be integrated into a single assembly, and be configured as a gearmotor. In some alternative examples, the drive element may drive the first spindle 215-*b* or the second spindle 225-*b* instead of the third spindle 335-*a*.

As shown in the schematic view of the first state 300-*a* of the illustrated example, the first spindle axis 216-*b* can be at a different height than the third spindle axis 336-*a*, and the second spindle axis 226-*b* can be at a different height than the third spindle axis 336-*a*. In various examples, each of the first spindle axis 216-*b*, the second spindle axis 226-*b*, and the third spindle axis 336-*a* can be at different heights, or they can each be at the same height. In other words, the first spindle axis 216-*b*, the second spindle axis 226-*b*, and the third spindle axis 336-*a* can all be coplanar, or non-coplanar. Furthermore, the first spindle 215-*b* and the second spindle 225-*b* can be on opposing sides of the third spindle 335-*a*.

In the illustrated example, the third spindle 335-*a* is coupled with the first spindle 215-*b* by way of a first pair of link arms 310-*a*, the first pair of link arms 310-*a* including a first link arm 330-*a*-1 and a second link arm 330-*a*-2. The third spindle 335 is also coupled with the second spindle 225-*b* by way of a second pair of link arms 320-*a*, the second pair of link arms 320-*a* including a third link arm 330-*b*-1 and a fourth link arm 330-*b*-2. Any of the link arms 330 can have either a fixed length or a variable length. The coupling of each of the link arms 330 to any of the first spindle 215-*b*, the second spindle 225-*b*, and the third spindle 335-*a* can provide a rotational degree of freedom at the coupling, such as the degree of freedom provided by a cylindrical bearing or a spherical bearing. Such bearings can be selected, for instance, to provide an efficient, low-friction interface between components to improve accuracy of antenna positioning, and/or to reduce the energy required of the drive element to provide antenna positioning.

As shown in the schematic view of the first state 300-*a* of the illustrated example, the first link arm 330-*a*-1 and the second link arm 330-*a*-2 can be parallel to each other, and separated by a first separation distance 311, and the third link arm 330-*b*-1 and the fourth link arm 330-2 can be parallel to each other, and separated by a second separation distance 321. In the illustrated example, the second separation distance 321 is different from the first separation distance 311. In other examples, the second separation distance 321 can be equal to the first separation distance 311.

In some examples, the first link arm 330-*a*-1 and the second link arm 330-*a*-2 can be non-parallel, and/or the third link arm 330-*b*-1 and the fourth link arm 330-*b*-2 can be non-parallel. In such examples where the first link arm 330-*a*-1 and the second link arm 330-*a*-2 are non-parallel, and/or the third link arm 330-*b*-1 and the fourth link arm 330-*b*-2 are non-parallel, the first spindle axis 216-*b* can be at a non-fixed location with respect to the third spindle axis 336-*a*, or the second spindle axis 226-*b* can be at a non-fixed location relative to the third spindle axis 336-*a*. Furthermore, in the present example, the first spindle axis 216-*b* can be parallel to the second spindle axis 226-*b*. In other examples, the first spindle axis 216-*b* and the second spindle axis 226-*b* can be non-parallel. A non-fixed location between any of the first spindle axis 216-*b*, the second spindle axis 226-*b*, and the third spindle axis 336-*a* can be provided by a kinematic linkage, or by an elastic member, such as an elastic link arm 330, an elastic bushing at a bearing location of any of the first spindle 215-*b*, the second spindle 225-*b*, and the third spindle 335-*a*, or another elastic member of the multiple-antenna positioner 270-*b*.

The first link arm 330-*a*-1 can have a coupling location at the third spindle 335-*a* at a first radial distance 312 and the third link arm 330-*b*-1 can have a coupling location at the third spindle 335-*a* at a second radial distance 322. In the present example, the second radial distance 322 is different from the first radial distance 312. In other examples, the second radial distance 322 can be the same as the first radial distance 312. In the present example, an angular location on the third spindle 335-*a* of a coupling between the first link arm 330-*a*-1 and the third spindle 335-*a* is different from an angular location on the third spindle 335-*a* of a coupling between the third link arm 330-*b*-1 and the third spindle 335-*a*. In other examples, an angular location on the third spindle 335-*a* of a coupling between the first link arm 330-*a*-1 and the third spindle 335-*a* be the same as an angular location on the third spindle 335 of a coupling between the third link arm 330-*b*-1 and the third spindle 335-*a*. That is, ends of the link arms 330-*a*-1 and 330-*b*-1 may be rotationally coupled with the third spindle 335-*a* about a same rotational axis.

When coupled in the manner of the illustrated example, the driven angular rotation of the third spindle 335-*a* simultaneously causes the angular rotation of both the first spindle 215-*b* and the second spindle 225-*b*, and consequently provides a simultaneous adjustment to the elevation angles of both the first antenna boresight 211-*b* and the second antenna boresight 221-*b*.

Figure 3B:
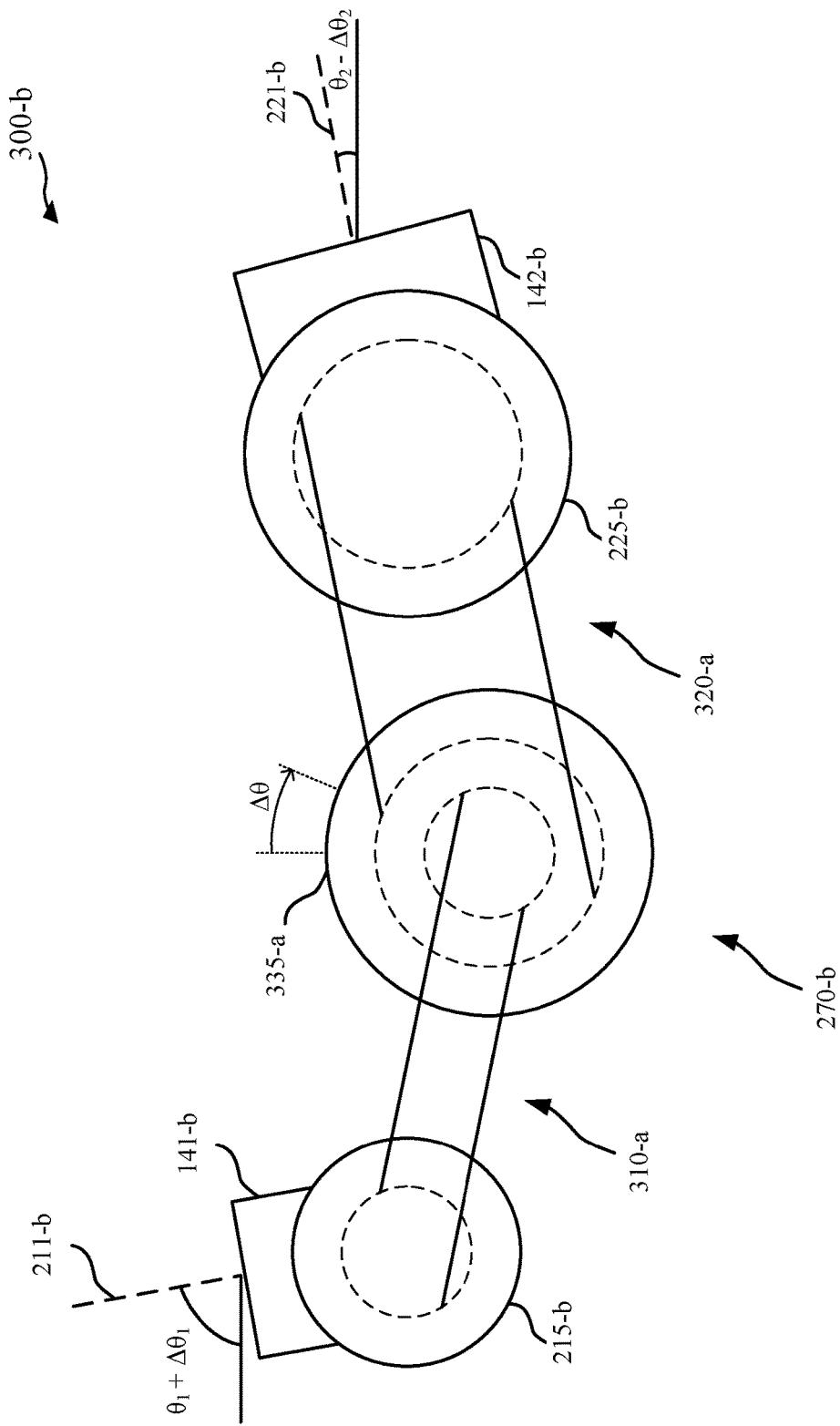
FIG. 3B shows a schematic view of a second state of a multiple-antenna positioner in accordance with various aspects of the present disclosure.

FIG. 3B shows a schematic view of a second state 300-*b* of the multiple-antenna positioner 270-*b* in accordance with various aspects of the present disclosure. In the second state of the illustrated example, for instance, the third spindle 335-*a* can have a driven angular rotation equal to $\Delta\theta$ compared to the schematic view of the first state 300-*a* in FIG. 3A. The driven angular rotation can, for instance, direct the first antenna boresight 211-*b* towards a satellite to establish or maintain a communications link using the first antenna 141-*b*, or direct the second antenna boresight 221-*b* towards a satellite to establish or maintain a communications link using the second antenna 142-*b*. For example, the driven angular rotation can be determined by an antenna control unit to provide an initial adjustment to the elevation angle of the first antenna boresight 211-*b* to establish a communications link with a satellite using the first antenna 141-*b*. The driven angular rotation can then be determined by the antenna control unit to maintain the communications link with the satellite over time by compensating for movement of the satellite and/or a vehicle carrying the multiple-antenna positioner, such as an aircraft.

As shown, the driven angular rotation can simultaneously cause an angular rotation of the first spindle 215-*b* equal to $\Delta\theta_1$ and an angular rotation of the second spindle 225-*b* equal to $\Delta\theta_2$. Compared to the schematic view of the first state 300-*a* in FIG. 3A, the driven angular rotation can increase an elevation angle of the first antenna boresight 211-*b* to an elevation angle equal to $\theta_1+\Delta\theta_1$, and the driven angular rotation can decrease an elevation angle of the second antenna boresight 221-*b* to an angle equal to $\theta_2-\Delta\theta_2$. In some examples, $\Delta\theta_1$ can be equal to $\Delta\theta_2$, so that the increase in an elevation angle of the first antenna boresight 211-*b* can be equal to the decrease in an elevation angle of the second antenna boresight 221-*b*.

Some antenna positioning systems may exhibit a degree of backlash, which limits the accuracy and/or responsiveness of the positioning of an antenna boresight. With respect to the present example, a degree of backlash can refer, for example, to an amount of driven rotation of the third spindle 335-*a* which does not result in an immediate rotation of the first spindle 215-*b* and/or the second spindle 225-*b*. A degree of backlash can also refer to an amount of uncontrolled rotation of either of the first spindle 215-*b* or the second spindle 225-*b*, which allows an elevation angle of the first antenna boresight 211-*b* or the second antenna boresight 221-*b* to change despite the third spindle 335-*a* being held in a fixed position.

A degree of backlash can be caused by, for instance, a loose mechanical fit. A loose mechanical fit may be caused by a shaft or bearing being loose in a collar, a rolling bearing element being smaller than the corresponding gap between two bearing races, a fastener being smaller than a hole for the fastener, or any other cause of two mechanical components lacking direct contact. The loose mechanical fit may be a result at least one of the design of various components of the multiple-antenna positioner 270-*b*, the manufacture of various components of the multiple-antenna positioner 270-*b*, or the degradation of various components of the multiple-antenna positioner 270-*b* over time.

At least one of the first link arm 330-*a*-1, the second link arm 330-*a*-2, the third link arm 330-*b*-1, or the fourth link arm 330-*b*-2 can be adjusted to reduce a degree of backlash between the third spindle 335-*a* and at least one of the first spindle 215-*b* or the second spindle 225-*b*. For example, first pair of link arms 310-*a*, comprising the first link arm 330-*a*-1 and the second link arm 330-*a*-2, which couple the third spindle 335-*a* to the first spindle 215-*b*, can be adjusted to reduce a degree of backlash between the third spindle 335-*a* and the first spindle 215-*b*, which may be the result of a looseness in mechanical fit between various components of the multiple-antenna positioner 270-*b*.

The looseness of mechanical fit between various components of the multiple-antenna positioner 270-*b* that contribute to the degree of backlash between the third spindle 335-*a* and the first spindle 215-*b* can, for instance, be a result of at least one of a coupling gap between the first spindle 215-*b* and the first link arm 330-*a*-1, a coupling gap between the first spindle 215-*b* and the second link arm 330-*a*-2, a coupling gap between the third spindle 335-*a* and the first link arm 330-*a*-1, or a coupling gap between the third spindle 335-*a* and the second link arm 330-*a*-2. The looseness of mechanical fit between various components of the multiple-antenna positioner 270-*b* that contribute to the degree of backlash between the third spindle 335-*a* and the first spindle 215-*b* can also include at least one of a loose or worn bearing of the first spindle 215-*b*, or a loose or worn bearing of the third spindle 335-*a*. The looseness of mechanical fit between various components of the multiple-antenna positioner 270-*b* that contribute to the degree of backlash between the third spindle 335-*a* and the first spindle 215-*b* can be a result a non-constrained positioning of a bearing of the first spindle 215-*b* or a non-constrained positioning of a bearing of the third spindle 335-*a*, where some other means of constraining the mechanical location is required.

To reduce a degree of backlash between the third spindle 335-*a* and the first spindle 215-*b*, the first pair of link arms 310-*a* can be adjusted to reduce, for instance, the looseness of mechanical fit between various components of the multiple-antenna positioner 270-*b*. For example, at least one of the first link arm 330-*a*-1 or the second link arm 330-*a*-2 can be adjusted to a longer length, which can reduce gaps between various components of the multiple-antenna positioner 270-*b*. Alternatively, at least one of the first link arm 330-*a*-1 or the second link arm 330-*a*-2 can be adjusted to a shorter length, which can also reduce gaps between various components of the multiple-antenna positioner 270-*b*. An adjustment to the length of the first link arm 330-*a*-1 and/or the second link arm 330-*a*-2 can be provided by a turnbuckle mechanism as described in greater detail with reference to FIG. 5. Alternatively, an adjustment to the length of the first link arm 330-*a*-1 and/or the second link arm 330-*a*-2 can be provided by any other suitable mechanism such as a jack screw, a gear screw, a worm gear, a hydraulic or pneumatic cylinder, a linear actuator, and the like.

A degree of backlash may also refer to a level of preload in a portion of the multiple-antenna positioner 270-*b*. For instance, at least one of the first link arm 330-*a*-1 or the second link arm 330-*a*-2 can be adjusted to a longer length, such that mechanical gaps between various components of the multiple-antenna positioner 270-*b* are eliminated, substantially eliminating backlash between the third spindle 335-*a* and the first spindle 215-*b*. At least one of the first link arm 330-*a*-1 or the second link arm 330-*a*-2 can be further adjusted to an incrementally longer length, which can cause both the first link arm 330-*a*-1 and the second link arm 330-*a*-2 to carry a compressive preload. The compressive preload of the first link arm 330-*a*-1 and the second link arm 330-*a*-2 can be resolved by, for instance, a corresponding tensile preload in a structure that supports the first spindle 215-*b* and the second spindle 225-*b*, such as the spindle support structure 265 described with respect to FIGS. 2A and 2B. The compressive preload of the first link arm 330-*a*-1 and the second link arm 330-*a*-2 can maintain the eliminated backlash between the third spindle 335-*a* and the first spindle 215-*b* over time by compensating for the wear of various components of the multiple-antenna positioner 270-*b* over time. This compensation over time is a result of the elasticity of elastic components in the multiple-antenna positioner 270-*b*, which have a first size at an initial degree of compressive preload, and a second size at a reduced degree of compressive preload. As various components of the multiple-antenna positioner 270-*b* experience wear over time, elastic components of the multiple-antenna positioner 270-*b* can compensate by changing from a first size to a second size, which reduces the degree of compressive preload in the first link arm 330-*a*-1 and the second link arm 330-*a*-2, but maintains the eliminated backlash between the third spindle 335-*a* and the first spindle 215-*c* over time. Although not described in detail, third link arm 330-*b*-1 and/or fourth link arm 330-*b*-2 may be similarly adjusted to, for example, reduce a degree of backlash between the second spindle 225-*b* and the third spindle 335.

In some examples, at least one of the first link arm 330-*a*-1 or the second link arm 330-*a*-2 can be adjusted to a shorter length, such that mechanical gaps between various components of the multiple-antenna positioner 270-*b* are eliminated, substantially eliminating backlash between the third spindle 335-*a* and the first spindle 215-*b*. At least one of the first link arm 330-*a*-1 or the second link arm 330-*a*-2 can be further adjusted to an incrementally shorter length, which can cause both the first link arm 330-*a*-1 and the second link arm 330-*a*-2 to carry a tensile preload. The tensile preload of the first link arm 330-*a*-1 and the second link arm 330-*a*-2 can be resolved by, for instance, a corresponding compressive preload in a structure that supports the first spindle 215-*b* and the second spindle 225-*b*, such as the spindle support structure 265 described with respect to FIGS. 2A and 2B. The compressive preload of the first link arm 330-*a*-1 and the second link arm 330-*a*-2 can maintain the eliminated backlash between the third spindle 335-*a* and the first spindle 215-*b* over time by compensating for the wear of various components of the multiple-antenna positioner 270-*b* over time. This compensation over time is a result of the elasticity of elastic components in the multiple-antenna positioner 270-*b*, which have a first size at an initial degree of tensile preload, and a second size at a reduced degree of tensile preload. As various components of the multiple-antenna positioner 270-*b* experience wear over time, elastic components of the multiple-antenna positioner 270-*b* can change from a first size to a second size, which reduces the degree of tensile preload, but maintains the eliminated backlash between the third spindle 335-*a* and the first spindle 215-*b* over time. Although not described in detail, third link arm 330-*b*-1 and/or fourth link arm 330-*b*-2 may be similarly adjusted to, for example, reduce a degree of backlash between the second spindle 225-*b* and the third spindle 335-*a*.

In some examples, both the first pair of link arms 310-*a*, and the second pair of link arms 320-*a* can be adjusted to a compressive preload as described above. In other examples, both the first pair of link arms 310-*a* and the second pair of link arms 320-*a* can be adjusted to a tensile preload as described above. In some examples, one of the first pair of link arms 310-*a* and the second pair of link arms 320-*a* can be adjusted to a tensile preload, and the other can be adjusted to a compressive preload as described above. By way of any of these methods, a degree of backlash in the multiple-antenna positioner 270-*b* can be reduced.

In some examples, it may therefore be desirable to select a particular degree of component elasticity to balance a level of preload of the multiple-antenna positioner 270-*b* with a level of wear to be compensated. This selection may further include the consideration of a mechanical load applied to a bearing of the first spindle 215-*b*, a mechanical load applied to a bearing of the second spindle 225-*b*, and/or a mechanical load applied to a bearing of the third spindle 335-*a*. In an example, the selection of a particular degree of elasticity may be specifically directed towards the selection of an elasticity of at least one of the first link arm 330-*a*-1, the second link arm 330-*a*-2, the third link arm 330-*b*-1, and the fourth link arm 330-*b*-2, where the degree of elasticity can be a combination of material properties and component geometry.

By reducing a degree of backlash in the multiple-antenna positioner 270-*b*, the multiple-antenna positioner can have a favorable degree of stiffness, such that the accuracy and/or responsiveness of the positioning of an antenna boresight is improved. For instance, the reduction in backlash can improve the responsiveness of the first antenna boresight 211-*b* and/or the second antenna boresight 221-*b* to a driven angular rotation equal to $\Delta\theta$ of the third spindle 335-*a*. The reduction of backlash can also reduce an amount of uncontrolled rotation of either of the first spindle 215-*b* or the second spindle 225-*b* while the third spindle 335 is held in a fixed position, helping to maintain an elevation angle of the first antenna boresight 211-*b* or the second antenna boresight 221-*b*.

Figure 4A:
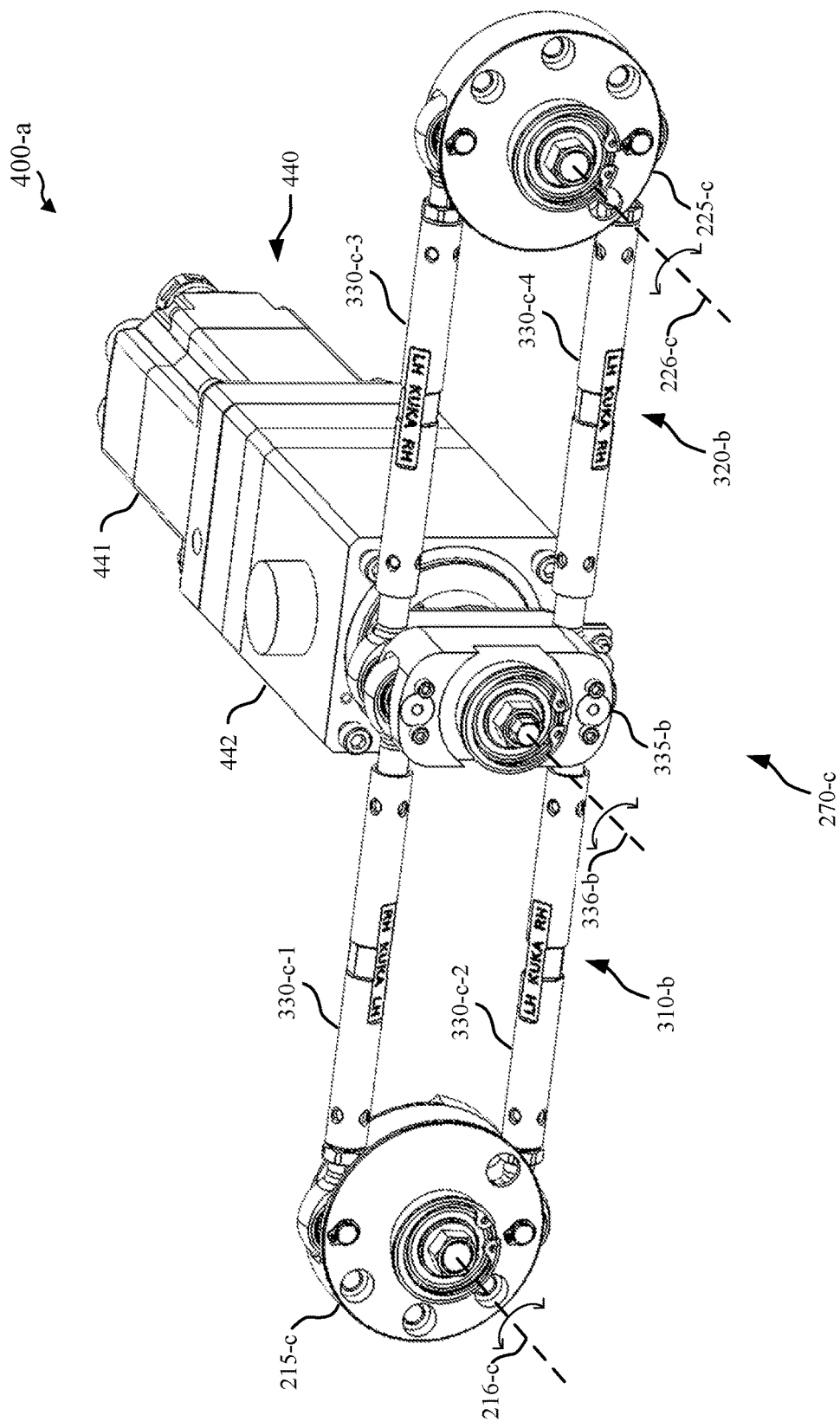
FIG. 4A shows a view of a multiple-antenna positioner in accordance with various aspects of the present disclosure.

FIG. 4A shows a first view 400-*a* of a multiple-antenna positioner 270-*c* in accordance with various aspects of the present disclosure. The multiple-antenna positioner 270-*c* may illustrate aspects of the multiple-antenna positioners 270 of FIG. 2A, 2B, 3A, or 3B. The multiple-antenna positioner 270-*c* includes a first spindle 215-*c* which is coupled with a first antenna (e.g., antennas 141 of FIG. 1, 2A, 2B, 3A or 3B, etc.), and a second spindle 225-*c* which is coupled with a second antenna (e.g., antennas 142 of FIG. 1, 2A, 2B, 3A or 3B, etc.). The multiple-antenna positioner includes a third spindle 335-*b*, which rotates about third spindle axis 336-*a* and is coupled with a drive element 440. The drive element 440 may include any element suitable for rotating the third spindle 335-*b*, which in some examples may include a motor 441, and may further include a gearbox 442. The motor 441 may be any motor suitable for providing a rotation of the third spindle, including an AC electrical motor, a DC electrical motor, a hydraulic motor, or any other suitable motor. The gearbox 442 may be any mechanism suitable for providing a mechanical ratio between the motor and the third spindle 335-*b*, any may include any of a bevel gear, a helical gear, a worm gear, a clutch, a hydraulic transmission, and any other suitable mechanism. In some examples the motor 441 and the gearbox 442 can be integrated into a single assembly, and be configured as a gearmotor. In some examples, the drive element 440 may drive the first spindle 215-*c* or the second spindle 225-*c* instead of the third spindle 335-*b*.

In the present example, the third spindle 335-*b* is coupled with the first spindle 215-*c* by way of a first pair of link arms 310-*b*, the first pair of link arms 310-*b* including a first link arm 330-*c*-1 and a second link arm 330-*c*-2. When coupled in this manner, a driven angular rotation of the third spindle 335-*b* causes an angular rotation of the first spindle 215-*c*. The third spindle 335-*b* is also coupled with the second spindle 225-*c* by way of a second pair of link arms 320-*b*, the second pair of link arms 320-*b* including a third link arm 330-*c*-3 and a fourth link arm 330-*c*-4. When coupled in this manner, a driven angular rotation of the third spindle 335 also causes an angular rotation of the second spindle 225-*c*. Therefore, in the present example, the driven angular rotation of the third spindle 335-*b* simultaneously causes the angular rotation of both the first spindle 215-*c* and the second spindle 225-*c*, and consequently provides a simultaneous adjustment to the elevation angle of both a first antenna boresight 211 of a first antenna 141 and a second antenna boresight 221 of a second antenna 142.

In some examples of the multiple-antenna positioner 270-*c*, it may be desirable to have various components of the multiple-antenna positioner 270-*c* be removably coupled with one another. Furthermore, it may be desirable to be able to remove a single component of the multiple-antenna positioner 270-*c* for repair or replacement without removing any of the other components of the multiple-antenna positioner 270-*c*. For instance, a multiple-antenna positioner 270-*c* can be configured such that any one of the first link arm 330-*c*-1, the second link arm 330-*c*-2, the third link arm 330-*c*-3, or the fourth link arm 330-*c*-4 is removable without removing any of the first spindle 215-*c*, the second spindle 225-*c*, the third spindle 335, or the drive element 440. These components may be removably coupled by way of various fastening techniques, such as a press-fit pin/axle, a pin/axle with an axially threaded portion, a bearing housing secured with one or more screws or bolts, an axle with a cotter pin, or any other known method of providing mechanical attachment. A multiple-antenna positioner 270-*c* can also be configured, for instance, such that the drive element 440 is removable without removing any of the first link arm 330-*c*-1, the second link arm 330-*c*-2, the third link arm 330-*c*-3, the fourth link arm 330-*c*-4 the first spindle 215-*c*, the second spindle 225-*c*, or the third spindle 335-*b*.

Figure 4B:
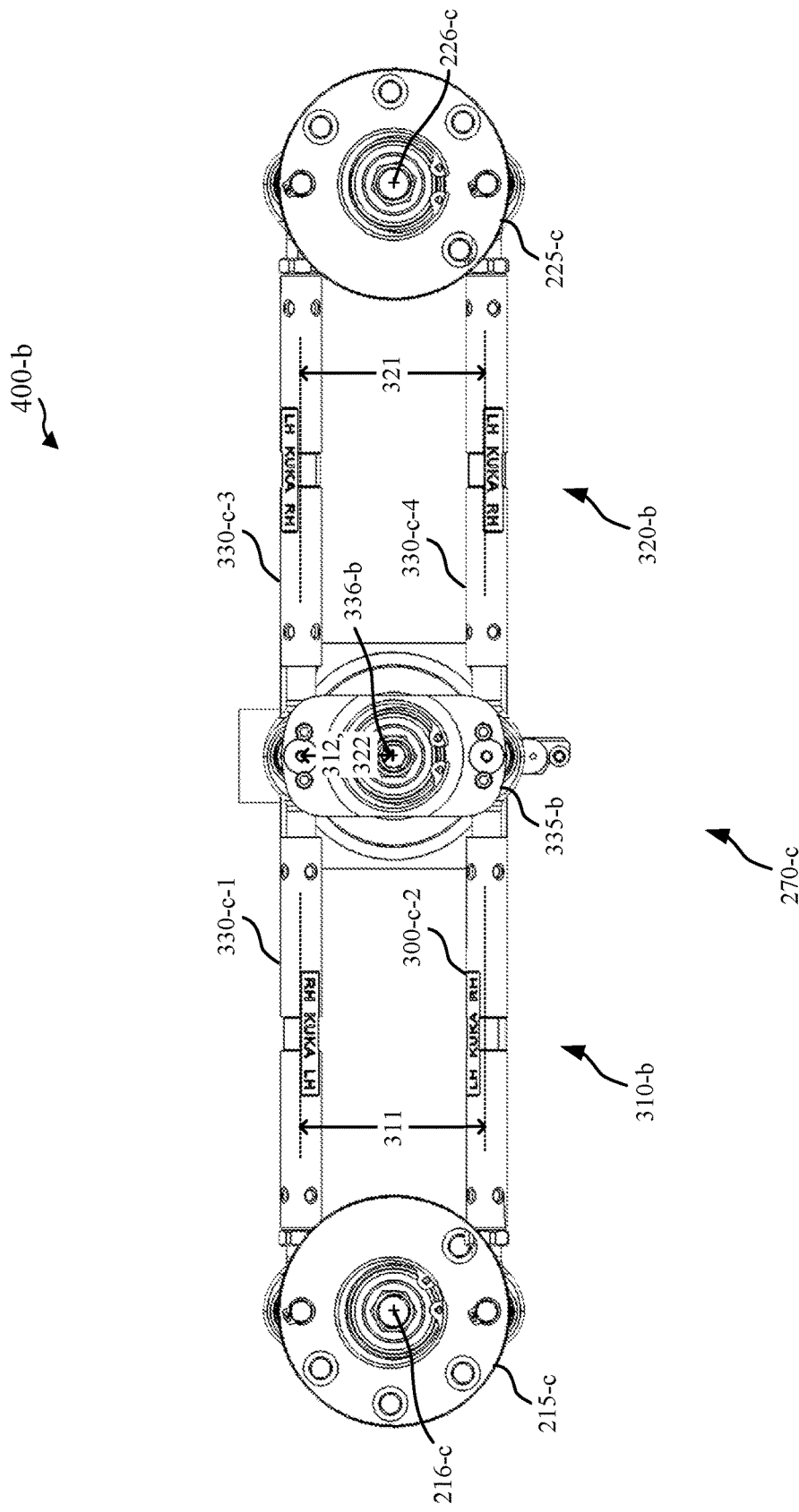
FIG. 4B shows an alternate view of the multiple-antenna positioner in accordance with various aspects of the present disclosure.

FIG. 4B shows an second view 400-*b* of the multiple-antenna positioner 270-*c* in accordance with various aspects of the present disclosure, with the view in line with the first spindle axis 216. As shown in view 400-*b*, the first link arm 330-*c*-1 and the second link arm 330-*c*-2 are parallel to each other, and separated by a first separation distance 311. Furthermore, first link arm 330-*c*-1 can have a coupling location at the third spindle 335-*b* at a first radial distance 312. In the illustrated example, the second spindle axis 226-*c* is parallel to the first spindle axis 216-*c*. The third link arm 330-*c*-3 and the fourth link arm 330-*c*-4 are parallel to each other, and separated by a second separation distance 321. In the illustrated example, the second separation distance 321 is the same as the first separation distance 311.

In other examples, the second separation distance 321 can be different from the first separation distance 311. Third link arm 330-*c*-3 can have a coupling location at the third spindle 335-*b* at a second radial distance 322. In the illustrated example, the second radial distance 322 is the same as the first radial distance 312. In other examples, the second radial distance 322 can be different from the first radial distance 312. In the illustrated example, an angular location on the third spindle 335-*b* of a coupling between the first link arm 330-*c*-1 and the third spindle 335-*b* is the same as an angular location on the third spindle 335-*b* of a coupling between the third link arm 330-*c*-3 and the third spindle 335-*b*. In other examples, an angular location on the third spindle 335-*b* of a coupling between the first link arm 330-*c*-1 and the third spindle 335-*b* can be different from an angular location on the third spindle 335 of a coupling between the third link arm 330-*c*-3 and the third spindle 335-*b*.

In the present example, the first link arm 330-*c*-1, the second link arm 330-*c*-2, the third link arm 330-*c*-3, and the fourth link arm 330-*c*-4 are identical components. At least one of the first link arm 330-*c*-1, the second link arm 330-*c*-2, the third link arm 330-*c*-3, or the fourth link arm 330-*c*-4 can be adjusted to reduce a degree of backlash between the third spindle 335 and at least one of the first spindle 215-*c* or the second spindle 225-*c*, as previously described with respect to multiple-antenna positioners 270 of FIGS. 3A, 3B, and 4A. By reducing the degree of backlash, the multiple-antenna positioner 270-*c* can have a favorable degree of stiffness, such that the positioning of each of the antennas can be more responsive to a rotation of the drive spindle, and can also be more stable when the drive spindle is held in a fixed position.

In some examples, the operating temperature for the multiple-antenna positioner 270-*c* may change over time. In such examples, it may be desirable to limit the adverse effects of thermal expansion of various components of the multiple-antenna positioner 270-*c*. This may be accomplished, for instance, by using the same material for various components of the multiple-antenna positioner 270-*c*. For example, the first spindle 215-*c*, the second spindle 225-*c*, the third spindle 335-*b*, the first pair of link arms 310-*b*, and the second pair of link arms 320-*b* may all be formed substantially by stainless steel, so that each of those components expand together, and contract together, as the operating temperature for the multiple-antenna positioner 270-*c* changes over time.

Figure 5:
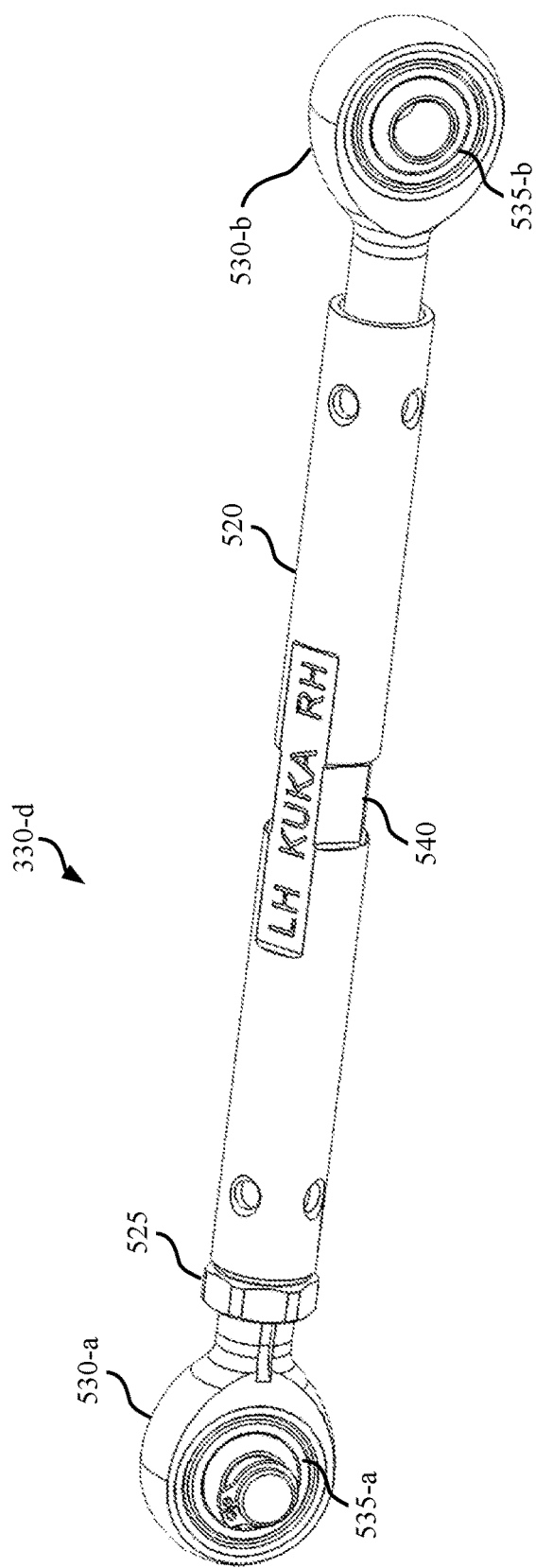
FIG. 5 shows an example of a link arm in accordance with various aspects of the present disclosure.

FIG. 5 shows an example of a link arm 330-*d* in accordance with various aspects of the present disclosure. The link arm 330-*d* can include a body portion 520, a first bearing rod end 530-*a* and a second bearing rod end 530-*b*. The body portion 520 can have internal threads at a first end to receive an externally threaded portion of the first bearing rod end 530-*a*. The body portion 520 can also have internal threads at a second end to receive an externally threaded portion of the second bearing rod end 530-*b*. The externally threaded portion of the first bearing rod end 530-*a* can be a left-handed thread, and the externally threaded portion of the second bearing rod end 530-*b* can be a right-handed thread. In this manner, the body portion 520, the first bearing rod end 530-*a*, and the second bearing rod end 530-*b* can combine to form a turnbuckle assembly.

When the link arm 330-*d* is configured as a turnbuckle assembly, a rotation of the body portion 520 along the axis between the first bearing rod end 530-*a* and the second bearing rod end 530-*b*, without a similar rotation of the first bearing rod end 530-*a* or the second bearing rod end 530-*b*, can cause a lengthening or shortening of the link arm 330-*d*. Specifically, the first bearing rod end 530-*a* and the second bearing rod end 530-*b* can be forced closer together, or farther apart. The rotation of the body portion 520 can be facilitated by a flat section 540, which can be configured to accept a wrench, or other suitable tool. To prevent unwanted rotation of the body portion 520, the link arm 330-*d* can also include a lock nut 525, engaged on the externally-threaded portion of the first bearing rod end 530-*a*, for instance. The lock nut 525 can be tightened onto the body portion 520, while the body portion 520 and the first bearing rod end 530-*a* are prevented from rotating, to provide a preload that prevents unwanted rotation of the body portion 520, which may lead to unwanted lengthening or shortening of the link arm 330-*d*.

The first bearing rod end 530-*a* and the second bearing rod end 530-*b* can include a first bearing 535-*a* and a second bearing 535-*b*, respectively. One or both of the first bearing 535-*a* and second bearing 535-*b* can be a cylindrical bearing to provide a rotational degree of freedom between the link arm 330-*d* and a spindle of a multiple-antenna positioning system, as described with respect to first spindles 215, second spindles 225, third spindles 335, and link arms 330 in FIG. 2A, FIG. 2B, FIG. 3A, FIG. 3B, FIG. 4A, and FIG. 4B. A cylindrical bearing can be any roller bearing, such as those that use ball bearings, cylindrical rolling elements, or spherical rolling elements, or alternatively the cylindrical bearing can be a sleeve bushing. The rotational degree of freedom can, for instance, reduce friction and/or reduce wear between coupled components, and thereby reduce the torque required of the drive element 440 to rotate the first spindle 215-*c* and the second spindle 225-*c*, and also reduce the propensity for a degree of backlash to increase over time.

One or both of the first bearing 535-*a* and 535-*b* may alternatively be a spherical bearing, such as a ball joint, to provide a spherical degree of freedom. The spherical degree of freedom, in addition to providing the rotational degree of freedom required by the multiple-antenna positioners 270-*b* and 270-*c*, can also provide a further degree of freedom that can, for example, compensate for misalignment. The spherical degree of freedom can also provide for a configuration where a first spindle axis 216, a second spindle axis 226, and a third spindle axis 336 are non-parallel.

The link arm 330-*d* can be designed to have a certain elasticity, as described with respect to link arms 330 of FIG. 3B. For instance, any of the body portion 520, the first bearing rod end 530-*a*, and the second bearing rod end 530-*b* can be made from a material that has a suitable modulus of elasticity. Furthermore, any of the body portion 520, the first bearing rod end 530-*a*, and the second bearing rod end 530-*b* can have a geometry that provides a suitable elasticity. Suitable geometry may include a cross section through a part, a length of a part, or any portion of a part that provides suitable elasticity in a localized region.

The detailed description set forth above in connection with the appended drawings describes exemplary embodiments and does not represent the only embodiments that may be implemented or that are within the scope of the claims. The term "example" used throughout this description means "serving as an example, instance, or illustration," and not "preferred" or "advantageous over other embodiments." The detailed description includes specific details for the purpose of providing an understanding of the described techniques. These techniques, however, may be practiced without these specific details. In some instances, well-known structures and devices are shown in block diagram form in order to avoid obscuring the concepts of the described embodiments.

The foregoing description and claims may refer to elements or features as being "connected" or "coupled" together. As used herein, unless expressly stated otherwise, "connected" means that one element/feature is directly or indirectly connected to another element/feature. Likewise, unless expressly stated otherwise, "coupled" means that one element/feature is directly or indirectly coupled with another element/feature. Thus, although the various schematics shown in the Figures depict example arrangements of elements and components, additional intervening elements, devices, features, or components may be present in an actual embodiment (assuming that the functionality of the depicted circuits is not adversely affected).

Information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The functions described herein may be implemented in various ways, with different materials, features, shapes, sizes, or the like. Other examples and implementations are within the scope of the disclosure and appended claims. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates a disjunctive list such that, for example, a list of "at least one of A, B, or C" means A or B or C or AB or AC or BC or ABC (i.e., A and B and C).

The previous description of the disclosure is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not to be limited to the examples and designs described herein but is to be accorded the widest scope consistent with the principles and novel features disclosed herein.

What is claimed is:

1. An antenna assembly, comprising:
   a first antenna rotatably coupled with a support structure about a first axis, the first antenna having a first boresight;
   a second antenna rotatably coupled with the support structure about a second axis, the second antenna having a second boresight that is not parallel with the first boresight; and
   a drive element coupled with the first antenna and the second antenna and operable to simultaneously rotate the first antenna about the first axis and rotate the second antenna about the second axis.

2. The antenna assembly of claim 1, wherein the drive element is coupled with the first antenna by a first linkage and the drive element is coupled with the second antenna by a second linkage.

3. The antenna assembly of claim 1, wherein the coupling between the drive element and the first antenna is operable to change a degree of backlash between the drive element and the first antenna, or the coupling between the drive element and the second antenna is operable to change a degree of backlash between the drive element and the second antenna, or both.

4. The antenna assembly of claim 1, wherein the coupling between the drive element and the first antenna is operable to change a degree of preload between the drive element and the first antenna, or the coupling between the drive element and the second antenna is operable to change a degree of preload between the drive element and the second antenna, or both.

5. The antenna assembly of claim 1, wherein the first axis and the second axis are parallel.

6. The antenna assembly of claim 1, wherein the first axis and the second axis are not parallel.

7. The antenna assembly of claim 1, wherein the first axis and the second axis are both associated with a positioning degree of freedom, and simultaneously rotating the first antenna to cause a positive change with respect to the positioning degree of freedom causes a negative change with respect to the positioning degree of freedom for the second antenna.

8. The antenna assembly of claim 1, wherein the first axis and the second axis are both associated with a positioning degree of freedom, and simultaneously rotating the first antenna and the second antenna causes a positive change with respect to the positioning degree of freedom for both the first antenna and the second antenna, or causes a negative change with respect to the positioning degree of freedom for both the first antenna and the second antenna.

9. The antenna assembly of claim 1, wherein the first antenna is configured to operate over a first frequency band, and the second antenna is configured to operate over a second frequency band that is different from the first frequency band.

10. The antenna assembly of claim 1, further comprising:
    a base element rotatably coupled with the support structure about a third axis that is not parallel to the first axis and not parallel to the second axis; and
    a second drive element to rotate the support structure about the base element.

11. The antenna assembly of claim 1, further comprising:
    an antenna control unit operable to cause the antenna assembly to:
    track a first satellite with the drive element for communications via the first antenna; and
    track a second satellite with the drive element for communications via the second antenna.

12. The antenna assembly of claim 11, wherein the antenna control unit is operable to determine to switch between communications via the first antenna and communications via the second antenna.

13. The antenna assembly of claim 12, wherein the antenna control unit is operable to determine to switch between communications via the first antenna and communications via the second antenna based at least in part on a change of position of the antenna assembly.

14. The antenna assembly of claim 12, wherein the antenna control unit is operable to determine to switch between communications via the first antenna and communications via the second antenna based at least in part on a network availability, a communication capacity, or a communication cost, or a combination thereof.

15. The antenna assembly of claim 12, wherein the antenna control unit is operable to determine to switch between communications via the first antenna and communications via the second antenna based at least in part on an error condition or a fault condition.

16. The antenna assembly of claim 12, wherein the antenna control unit is operable to determine to switch between communications via the first antenna and communications via the second antenna based at least in part on a degradation of communications via the first antenna.

17. The antenna assembly of claim 11, wherein the first satellite and the second satellite are different satellites.

18. The antenna assembly of claim 11, wherein the first satellite and the second satellite are the same satellite.

19. A method of communication, comprising:
providing an antenna assembly having a first antenna rotatably coupled with a support structure about a first axis, a second antenna rotatably coupled with the support structure about a second axis, and a drive element coupled with the first antenna and the second antenna and operable to simultaneously rotate the first antenna about the first axis and rotate the second antenna about the second axis, wherein a boresight of the first antenna is non-parallel with a boresight of the second antenna;
tracking a first satellite with the drive element for communications via the first antenna;
determining to switch from communications via the first antenna to communications via the second antenna; and
tracking a second satellite with the drive element for communications via the second antenna.

20. The method of claim 19, wherein determining to switch from communications via the first antenna to communications via the second antenna is based at least in part on a change of position of the antenna assembly.

21. The method of claim 19, wherein determining to switch from communications via the first antenna to communications via the second antenna is based at least in part on a network availability, a communication capacity, a communication cost, or a combination thereof.

22. The method of claim 19, wherein determining wherein determining to switch from communications via the first antenna to communications via the second antenna is based at least in part on an error condition or a fault condition.

23. The method of claim 19, wherein determining to switch from communications via the first antenna to communications via the second antenna is based at least in part on a degradation of communications via the first antenna.

24. The method of claim 19, wherein the first satellite and the second satellite are the same satellite.

25. The method of claim 19, wherein the first satellite and the second satellite are different satellites.

* * * * *